Figure 1:
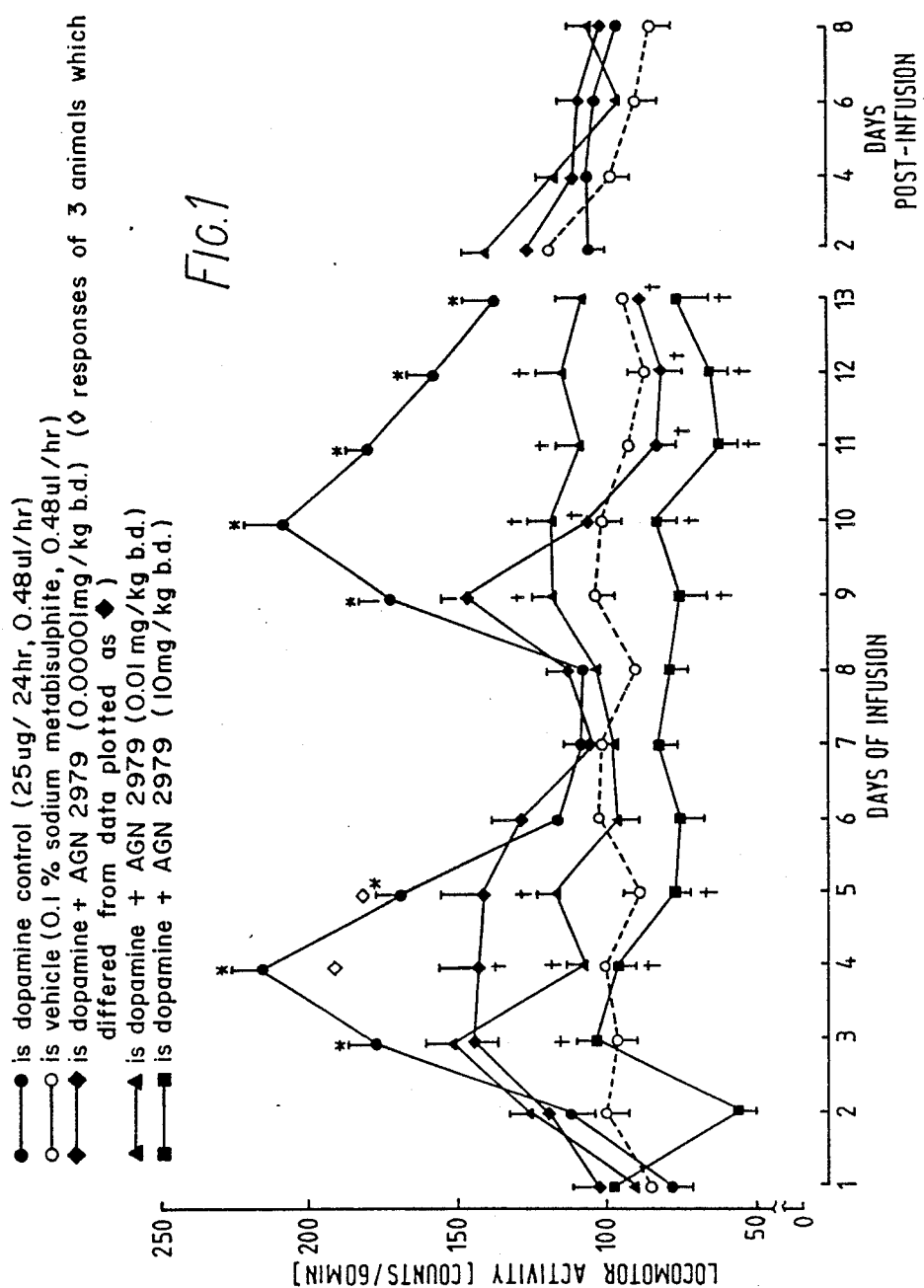

United States Patent

Costall

Patent Number: 4,877,800
Date of Patent: Oct. 31, 1989

[54] ANTIPSYCHOTIC COMPOSITIONS CONTAINING DIOXOPIPERIDINE DERIVATIVES

[75] Inventor: Brenda Costall, North Yorkshire, United Kingdom

[73] Assignee: National Research Development Corporation, London, England

[21] Appl. No.: 217,450

[22] Filed: Jul. 11, 1988

[30] Foreign Application Priority Data

Jul. 10, 1987 [GB] United Kingdom ................. 8716337

[51] Int. Cl.$^4$ ........................................... A61K 31/445
[52] U.S. Cl. .................................................... 514/328
[58] Field of Search ........................................ 514/328

[56] References Cited

FOREIGN PATENT DOCUMENTS 2181346A 4/1987 United Kingdom .

Primary Examiner—Stanley J. Friedman
Attorney, Agent, or Firm—Cushman, Darby & Cushman

[57] ABSTRACT

Phenyl-3-aminoalkyl-4-methyl-2,6-dioxopiperidines of the Formula I

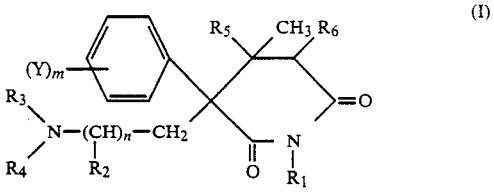

wherein:
  $R_1$ represents hydrogen or $C_1$–$C_4$ alkyl;
  n is 1 or 2;
  $R_2$ represents hydrogen or methyl, provided that one $R_2$ is hydrogen when n is 2;
  $R_3$ represents hydrogen or $C_1$–$C_2$ alkyl;
  $R_4$ represents $C_1$–$C_2$ alkyl;
  $R_5$ and $R_6$ independently represent hydrogen or methyl;
  m is 0 to 3; and each Y is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position, and pharmacologically acceptable salts thereof have antiposychotic activity without sedative side effects. They are particularly useful in the treatment of schizophrenia.

The presently preferred compound is 3-(3'methoxyphenyl)-3-(3''-N,N-dimethylaminopropyl) -4,4-dimethyl-2,6-dioxopiperidine (AGN 2979).

8 Claims, 2 Drawing Sheets

ANTIPSYCHOTIC COMPOSITIONS CONTAINING DIOXOPIPERIDINE DERIVATIVES

This invention relates to the use of certain 3-phenyl-3-aminoalkyl-4-methyl-2,6-dioxopiperidines as antipsychotic drugs. In particular, the invention provides the use of the said dioxopiperidines in the manufacture of antipsychotic medicaments and methods of treatment of psychosis using said dioxopiperidines.

Psychoses, including the schizophrenias and the bipolar manic-depressive stages, are presently treated by neuroleptic agents such as the phenothiazines or butyrophenones, or by lithium. However, these antipsychotic agents can cause undue motor depression and neurological disorders including Parkinson's disease and akasthisia. Further, long-term treatment with antischizophrenic agents can cause irreversible tardive dyskinesias.

Accordingly, there presently is a demand for compounds having strong antipsychotic activity without the side effects presently associated with antipsychotic therapy.

It has surprisingly now been found that certain 3-phenyl-3-aminoalkyl-4-methyl-2,6-dioxopiperidines (as defined hereinafter) have strong antipsychotic activity. Further, such actions appear to be independent of the side effects encountered with the presently used antipsychotic drugs.

GB No. 1455687 (also AU No. 480855, BE No. 808958, DE No. 23630526, FR No. 7346904, JP No. 6053014 and U.S. Pat. No. 3963729) discloses that 3-phenyl-3-aminoalkyl-4- and/or 5-methyl-2,6-dioxopiperidine derivatives have central nervous system, especially antidepressant, activity. Said compounds include, inter alia, those of the following Formula A.

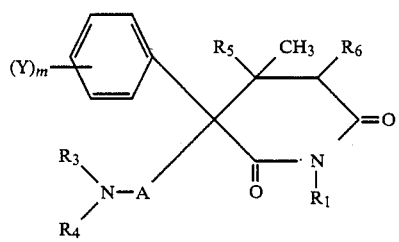

(A)

wherein:
$R_1$ represents hydrogen or $C_1$-$C_4$ alkyl;
$R_3$ represents hydrogen or C1-C4 alkyl;
$R_4$ represents C1-C4 alkyl;
$R_5$ and $R_6$ independently represent hydrogen or methyl;
A represents $C_1$-$C_6$ alkylene;
m is 0 to 3; and
Y is hydroxy, $C_1$-$C_4$ alkoxy, $C_1$-$C_4$ alkyl, $C_1$-$C_4$ hydroxyalkyl, halogen or trifluoromethyl.

The dose level specified for administration of the compounds is 0.1 to 100 mg/kg using pharmaceutical compositions containing 1 to 1000 mg per unit dose.

It also has been disclosed in U.S. Pat. No. 4,461,771 that compounds of Formula A, in which $R_1$ represents hydrogen; $R_3$ and $R_4$ independently represent methyl or ethyl; $R_5$ represents methyl; $R_6$ represents hydrogen; A represents ethylene or propylene; m is 1 or 2; and each Y is in a meta position and independently represents hydroxy or $C_1$-$C_2$ alkoxy, are believed to reduce in vitro the activity of tryptophan hydroxylase by blocking the depolarization-induced activation of the enzyme in the brain stem and hence are of potential use in the prophylatic treatment of the stressful disorder migraine. The dose level specified for this treatment is 0.01 to 10 mg/kg, especially 0.1 to 3 mg/kg, using pharmaceutical compositions containing 0.1 to 200 mg, usually 1 to 100 mg, per unit dose. More recently, it has been reported that at least one compound of Formula A (viz 3-(3'-methoxy-phenyl)-3-(3''-N,N-dimethylaminopropyl)-4,4-dimethyl-2,6-dioxopiperidine; AGN 2979) also blocks in vitro the activation of tryptophan hydroxylase resulting from exposure of brain stem slices to metabolic inhibitors or methylxanthines or induced by incubation of supernatant preparations of the enzyme under phosphorylating conditions (Boadle-Biber, M. C. et al Biochem. Pharmacol, 35, 1521-6, (1986)). However, it also has been reported that AGN 2979 has no significant effect in vitro upon the unactivated enzyme (Boadle-Biber, M. C. et al supra).

Further, it has recently been disclosed in GB No. 2181346A that compounds of Formula A, in which $R_1$ represents hydrogen; $R_3$ and $R_4$ independently represent methyl or ethyl; A represents ethylene or propylene; m is 1 or 2; and each Y is in a meta position and independently represents hydroxy or $C_1$-$C_2$ alkoxy, are believed to reduce the turnover of 5-hydroxytryptamine (5HT) resulting from inhibiting the activity of tryptophan hydroxylase. They are reported to have anxiolytic activity, antagonize the anxiogenic activity of benzodiazepines inverse agonists, reduce chronig abnormally high brain levels of 5HT or its metabolite 5-hydroxy-indoleacetic acid, and have antibacterial and antiviral activity.

G.B. No. 2181346A was published in pursuance of U.K. patent application No. 8621577 filed 8th Sept. 1986 and claiming prority from U.K. patent application Nos. 8522455 (filed 11th Sept. 1985), 8603909 (filed 17th Feb. 1986) and 8603910 (also filed 17th Feb. 1986). Originally, it was thought that the disclosed compounds were not themselves anxiolytic because they have virtually no action at benzodiazepine receptors and that they acted via some unknown pharmacological mechanism to potentiate the anxiolytic activity of benzodiazepine receptors. Their anxiolytic activity was disclosed for the first time in U.K. patent application No. 8621577. At that time, the compounds were believed to be active in the range 0.1 to 20 mg/kg, especially 0.5 to 10 mg/kg and hence pharmaceutical compositions containing 10 to 500 mg, especially 10 to 100 mg, were proposed. However, it has now surprisingly been found that the compounds are active at much lower dose levels, down to nanogram/kg amounts.

According to a first aspect of the present invention, there is provided the use in the manufacture of a medicament for the treatment of psychosis of a compound of the following Formula I.

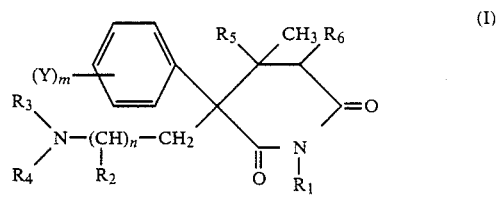

(I)

wherein:

$R_1$ represents hydrogen or $C_1$-$C_4$ alkyl;

n is 1 or 2;

$R_2$ represents hydrogen or methyl, provided that one $R_2$ is hydrogen when n is 2;

$R_3$ represents hydrogen or $C_1$-$C_2$ alkyl;

$R_4$ represents $C_1$-$C_2$ alkyl;

$R_5$ and $R_6$ independently represent hydrogen or methyl;

m is 0 to 3; and each Y is a meta or para position and independently represents hydroxy, $C_1$-$C_2$ alkoxy, $C_1$-$C_2$ alkyl, $C_1$-$C_2$ hydroxyalkyl, halogen, or trifluoromethyl, provided that hydroxy and alkoxy are not in the para position, or a pharmacologically acceptable salt thereof.

In a second aspect, the invention provides a method of treating a patient suffering from psychosis, which comprises administering to the patient an anti-psychotic effective amount of a compound of the following Formula I.

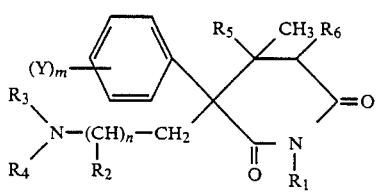

(I)

wherein:

$R_1$ represents hydrogen or $C_1$-$C_4$ alkyl;

n is 1 or 2;

$R_2$ represents hydrogen or methyl, provided that one $R_2$ is hydrogen where n is 2;

$R_3$ represents hydrogen or $C_1$-$C_2$ alkyl;

$R_4$ represents $C_1$-$C_2$ alkyl;

$R_5$ and $R_6$ independently represent hydrogen or methyl;

m is 0 to 3; and each Y is in a meta or para position and independently represents hydroxy, $C_1$-$C_2$ alkoxy, $C_1$-$C_2$ alkyl, $C_1$-$C_2$ hydroxyalkyl, halogen, or trifluoromethyl, provided that hydroxy and alkoxy are not in the para position, or a pharmacologically acceptable salt thereof.

The compounds of Formula I can be prepared in the manner disclosed in GB No. 1455687. They exist as optical isomers and can be used in racemate form or as individual (+) or (−) isomers. Presently, the (−) isomer is preferred.

As mentioned above the compounds of Formula 1 have antipsychotic activity and hence are useful in the treatment of psychosis. In particular, they antagonise the behavioural consequences of a raised mesolimbic dopamine function without sedation or depression of locomotor activity and without withdrawal problems, and are active over a wide dose range. Accordingly, they are of particular use in the treatment of schizophrenia. Other psychoses which can be treated by the compounds include manic depressive and other bipolar illnesses.

The compounds of Formula I can be administered in various manners to achieve the desired antipsychotic effect. The compounds can be administered enterally or parenterally to the patient being treated. Oral administration is likely to be the preferred route in most circumstances but injection, especially subcutaneously or intraveneously, will be preferred in some circumstances.

The amount of compound administered will vary and can be any anti-psychotic effective amount. Depending upon the patient and the mode of administration, the amount of compound administered may vary over a wide range to provide from about $10^{-7}$ to $10^2$ mg/kg, usually $10^{-5}$ to $10^2$ mg/kg, especially $10^{-4}$ to $10^2$ mg/kg, of body weight of the patient per unit dose. Unit doses of these compounds can contain, for example, from about $10^{-6}$ mg to 500 mg, usually $10^{-4}$ to $10^2$ mg, especially $10^{-3}$ to $10^2$ mg of the compound and may be administered, for example, from 1 to 4 times daily.

The term "unit dosage form" is used herein to mean a single or multiple dose form containing a quantity of the active ingredient in admixture with or otherwise in association with a diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

The compounds of Formula I have virtually no action at benzodiazepine receptors. The capacity of a selected number of compounds of Formula I to displace triturated flunitrazepam from benzodiazepine receptors has been measured with the results set forth in Table I below:

TABLE 1

| | COMPOUND OF FORMULA I | | | | |
|---|---|---|---|---|---|
| | 2979 | 3222 | 2939 | 3181 | DIAZEPAM* |
| IC50(uM) [³H]Flunitr-azepam Binding | 350 | 1300 | 9000 | 6700 | 0.014 |

*7-chloro-1,3-dihydro-1-methyl-5-phenyl-2H-1,4-benzodiazepine-2-one

The compounds of general Formula I can have the phenyl moiety substituted for one or both meta positions by $C_1$-$C_2$ alkyl, $C_1$-$C_2$ hydroxyalkyl, halogen, trifluoromethyl, or, preferably, hydroxy or $C_1$-$C_2$ alkoxy. Additionally or alternatively, the phenyl moiety can be substituted in the para position by the aforementioned groups other than hydroxy and alkoxy. It is presently preferred that the substituent(s) should be hydroxy or, especially, methoxy. It is also preferred that one or both meta positions are substituted and that, when there are two substituents, they should be the same.

The amino group of the compounds of Formula I can be secondary or tertiary having methyl or ethyl groups attached to the nitrogen atom. Dimethylamino presently is preferred. The amino group is connected to the piperidine ring by a divalent ethylene (i.e. n=1) or trimethylene (i.e. n=2) radical optionally substituted on a carbon atom not adjacent said ring with a methyl group. Presently, unsubstituted trimethylamine is preferred.

The piperidine ring of the compounds of Formula I is substituted in the 4-position with methyl and optionally by one or two further methyl groups in the 4 and/or 5 positions. It is presently preferred that there is one further methyl group in the 4 or 5 position, especially in the 4-position.

The ring nitrogen atom of the piperidine ring can be substituted with a $C_1$-$C_4$ alkyl group but it is presently preferred that said nitrogen atom is unsubstituted.

The $C_1$-$C_2$ alkyl groups or moieties referred to herein are methyl or ethyl; methyl present being preferred. The C3-C4 alkyl groups which may be substituents on the nitrogen atom of the piperidine ring can be straight or branched chain but the straight chain n-propyl or n-butyl groups presently are preferred. The halogen substituent(s) in the phenyl ring can be chlorine, bromine or fluorine; chlorine presently being preferred.

The present preferred compounds of Formula I are those of the following Formla IA.

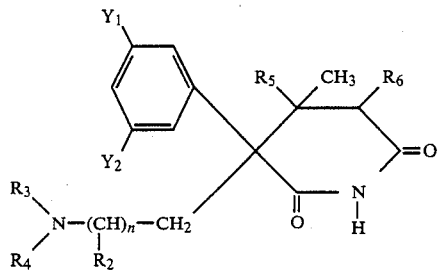

wherein:
n is 1 or 2;
$R_2$ represents hydrogen or methyl, provided that one $R_2$ is hydrogen when n is 2;
$R_3$ represents hydrogen or $C_1$–$C_2$ alkyl;
$R_4$ represents $C_1$–$C_2$ alkyl;
$R_5$ and $R_6$ independently represent hydrogen or methyl; and
$Y_1$ and $Y_2$ independently represent hydrogen, hydroxy or $C_1$–$C_2$ alkoxy, or a pharmacologically acceptable salt thereof.

The presently especially preferred compounds of Formula 1A are those of the following Formula IB.

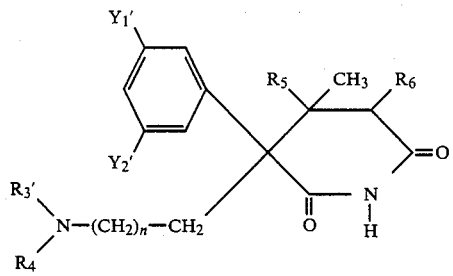

wherein:
n is 1 or 2;
$R_3'$ and $R_4$ independently represent $C_1$–$C_2$ alkyl;
$R_5$ and $R_6$ independently represen hydrogen or methyl;
$Y_1'$ represents hydroxy or $C_1$–$C_2$ alkoxy; and
$Y_2'$ represents hydrogen, hydroxy or $C_1$–$C_2$ alkoxy, or a pharmacologically acceptable salt thereof.

Examples of compounds of Formula IC include the following:
3-(3'-methoxyphenyl)-3-(2''-N,N-dimethylaminoethyl)-4,4-dimethyl-2,6-dioxopiperidine
3-(3'-methoxyphenyl)-3-(3''-N,N-dimethylaminopropyl)-4,4-dimethyl-2,6-dioxopiperidine (AGN 2979);
3-(3'-methoxyphenyl)-3-(2''-N,N-diethylaminoethyl)-4,4-dimethyl-2,6-dioxopiperidine;
3-(3'-methoxyphenyl)-3-(3''-N,N-diethylaminopropyl)-4,4-dimethyl-2,6-dioxopiperidine;
3-(3'-hydroxyphenyl)-3-(2''-N,N-dimethylaminoethyl)-4,4-dimethyl-2,6-dioxopiperidine;
3-(3'-hydroxyphenyl)-3-(3''-N,N-dimethylaminopropyl)-4,4-dimethyl-2,6-dioxopiperidine;
3-(3'-methoxyphenyl)-3-(2''-N,N-dimethylaminoethyl)-4,5-dimethyl-2,6-dioxopiperidine (AGN 2939);
3-(3'-methoxyphenyl)-3-(3''-N,N-dimethylaminopropyl)-4,5-dimethyl-2,6-dioxopiperidine (AGN 3181);
3-(3'-ethoxyphenyl)-3-(3''-N,N-dimethylaminopropyl)-4,4-dimethyl-2,6-dioxopiperidine;
3-(3'-ethoxyphenyl)-3-(3''-N,N-diethylaminopropyl)-4,4-dimethyl-2,6-dioxopiperidine;
3-(3',5'-dimethoxyphenyl)-3-(3''-N,N-dimethylaminopropyl)-4,4-dimethyl-2,6-dioxopiperidine (AGN 3222);
3-(3',5'-dimethoxyphenyl)-3-(2''-N,N-dimethylaminoethyl)-4,4-dimethyl-2,6-dioxopiperidine;
3-(3',5'-dimethoxy phenyl)-3-(3''-N,N-dimethylaminopropyl)-4,5-dimethyl-2,6-dioxopiperidine; and
3-(3',5'-dimethoxyphenyl)-3-(2''-N,N-dimethylaminoethyl)-4,5-dimethyl-2,6-dioxopiperidine;

Examples of other compounds of Formula I include:
3-phenyl-3-(2'-N,N-dimethylaminoethyl)-4-methyl-2,6-dioxopiperidine;
3-phenyl-3-(2'-N,N-dimethylaminoethyl)-4,4-dimethyl-2,6-dioxopiperidine;
3-phenyl-3-(2'-N,N-dimethylaminoethyl)-4,5-dimethyl-2,6-dioxopiperidine;
3-phenyl-3(3'-N,N-dimethylaminopropyl)-4,4-dimethyl-2,6-dioxopiperidine;
3-(4'-chlorophenyl)-3(3''-N,N-dimethylaminopropyl)-4,4-dimethyl-2,6-dioxopiperidine; and
3-phenyl-3(2'N-methylaminoethyl)-4,4-dimethyl-2,6-dioxopiperidine.

The compounds of Formula I may be administered in free base form, as an alkali metal or alkaline earth metal salt or as a pharmaceutically acceptable acid addition salt with the proviso that an alkali metal or alkaline earth metal salt is not normally combined with an acid addition salt except in a layer formulation. Representative acid addition salt forms include organic acid salt forms such as the maleate and methane sulphonate and mineral acid salt forms such as the hydrochloride and perchlorate.

The pharmaceutical formulations in which form the active compounds of the invention will normally be utilized are prepared in a manner well known per se in the pharmaceutical art and usually comprise at least one active compound of Formula I in admixture or otherwise in association with a pharmaceutically acceptable carrier or diluent therefor. For making those formulations the active ingredient will usually be mixed with a carrier, or diluted by a diluent, or enclosed or encaspulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations may be adapted for enteral or parenteral use and may be administered to the patient in the form of tablets, capsules, dragees, suppositories, syrups, suspensions, subcutaneous or intransmuscular depot injections or implants or the like. The formulations may be in delayed or sustained release form.

Aside from the active agents the compositions may contain pharmaceutically inert organic or inorganic adjuvants, optionally granulating agents, binding agents lubricants, dispersing agents, wetting agents and preservatives. Moreover, the pharmaceutical compositions may contain colouring, flavouring and sweetening substances. Adjuvants for the production of tablets may be e.g. calcium carbonate, lactose micro-crystalline cellulose, mannitol or talc. Starch and alginic acid or microcrystalline celluose may be used as granulating and disintegrating agents, starch, polyvinylpyrrolidone and gelatine may be used as binding agents and magnesium stearate, stearic acid, colloidal silica and talc as lubricants. Tablet formulation may be coated or uncoated, the coating having the purpose or delaying the disintegration and absorption in the gastrointestinal tract. Suitable suspending agents for the production of liquid administration forms are e.g. methyl cellulose and sodium alginate. Capsule formulation may contain the active agents on their own or together with an inert solid diluent e.g. calcium phosphate, corn starch, lactose, or mannitol.

The invention is illustrated in the following non-limiting Examples.

EXAMPLE 1

Tablet Formulation

Tablets each having the following composition are prepared by conventional techniques:

|  | mg/tablet |
|---|---|
| (a) Compound AGN 2979 base | 1 |
| (b) Lactose | 51.5 |
| (c) Maize starch dried | 45 |
| (d) Magnesium stearate | 1.5 |

EXAMPLE 2

Suppository Formulation

|  | mg/suppositiory |
|---|---|
| (a) Compound AGN 2979 HCl | 10 |
| (b) Oil of Theobroma (cocoa butter) | 990 |

The compound (a) is powdered and passed through a BS No. 100 sieve and triturated with molten oil of Theobroma at 45° C. to form a smooth suspensionn. The mixture is well stirred and poured into moulds each of nominal 1 G capacity to produce suppositories.

EXAMPLE 3

Tablet Formulation

| (a) Compound AGN 2979 base | 10 mg |
|---|---|
| (b) Wheat starch | 7 g |
| (c) Lactose | 20 g |
| (d) Magnesium Stearate | 1 g |

EXAMPLE 4

Pill Formulation

|  | per pill |
|---|---|
| (a) Compound AGN 2979 HCl | 10 mg |
| (b) Corn starch | 45 mg |
| (c) Liquid glucose | 7 ml |

The pills are prepared by blending the active ingredient (a) and the corn starch, then adding the liquid glucose with thorough kneading to form a plastic mass from which the pills are cut and formed.

EXAMPLE 5

Gelatine Capsule Formulation

|  | per capsule |
|---|---|
| (a) Compound AGN 2979 HCl | 2.5 mg |
| (b) Talc | 70 mg |

A capsule is prepared by passing dry powdered active ingredient (a) and powdered talc in the above proportions through a fine mesh screen and mixing them well. The powder is then filled into hard gelatin capsules at a net fill of 72.5 mg per capsule.

EXAMPLE 6

Male Sprague-Dawley (CD, Bradford strain) rats were used, weighing 300±25 g at the time of initial stereotaxic surgery.

The behavioural measure throughout was hyperactivity measured in individual photocell cages constructed by Perspex (Trade Mark), 25×15×15 cm high, each fitted with one photocell unit placed off-centre. The cages were screened. Interruptions of the light beams were continuously monitored and the level of locomoter activity expressed in counts/5 min.

Rats were subject to standard stereotaxic techniques for the implantation of chronically indwelling guide cannulae for subsequent bilateral intracerebral infusion into the centre of the nucleus accumbens (Ant. 9.4, Vert. 0.0, Lat. ±1.6, atlas of De Groot). Rats were anaesthetised with chloral hydrate (300 mg/kg s.c.) and placed in a Kopf stereotaxic instrument. Implanted guides were contructed of stainless steel 0.65 mm diameter, held bilaterally in Perspex holders. Guides terminated 3.5 mm above the centre of the nucleus accumbens and were kept patent for a 14-day recovery period using stainless steel stylets extending 0.5 mm beyond the guide tips.

After the 14 days recovery rats were anaesthetised with halothane/$N_2O$, $O_2$ for the s.c. implantation in the black region of two Alzet osmotic minipumps each attached via polyethene tubing, running subcutaneously, to stainless steel injection units (0.3 mm diameter) which were made to fit permanently into the previously implanted guides in place of the stylets, but terminating 3.5 mm below the guide tips at the centre of the nucleus accumbens. The pumps had previously been filled with dopamine solution (2.16 ug/ul, dopamine hydrochloride, Koch Light, prepared by $N_2$ bubbled solution containing 0.1% sodium metabisulphite), or its solvent, and the entire injection unit primed for between 5 and 8 h at 37° C. The pumps delivered dopamine or its solvent at a constant rate of 0.48 ul/hr from the time of implantation, and thus provided an intra-accumbens dose of dopamine of 25 ug over a 24 hr period. Pumps were removed on day 13. Rat spontaneous locomotion was measured between 8.00 and 11.00 a.m. AGN 2979 and fluphenazine were given twice daily at 7.30 a.m. and 7.30 p.m. Doses of AGN 2979 ranged from 0.00001–10 mg/kg i.p., fluphenazine from 0.002–0.05 mg/kg i.p.

FIG. 1 shows the antagonism by AGN 2979 of the hyperactivity caused by dopamine infused bilaterally into the rat nucleus accumbens. In this Figure:

●——● is dopamine control (25 ug/24 hr, 0.48 ul/hr)

○——○ is vehicle (0.1% sodium metabisulphite, 0.48 ul/hr)

◆——◆ is dopamine+AGN 2979 (0.00001 mg/kg b.d.) ( ◊ responses of 3 animals which differered from data plotted as ◆ )

▲——▲ is dopamine+AGN 2979 (0.01 mg/kg b.d.)

■——■ IS dopamine+AGN 2979 (10 mg/kg b.d.) n=6. S.E.M.s given. Significant elevation of locomotor activity by dopamine (compared to vehicle) is indicated as *P less than 0.001, whilst significant reduction in the dopamine hyperactivity by AGN 2979 is indicated at $_+$P less than 0.01-P less than 0.001 (two-way ANOVA followed by Dunnett's test for multiple comparisons).

Figure 2:
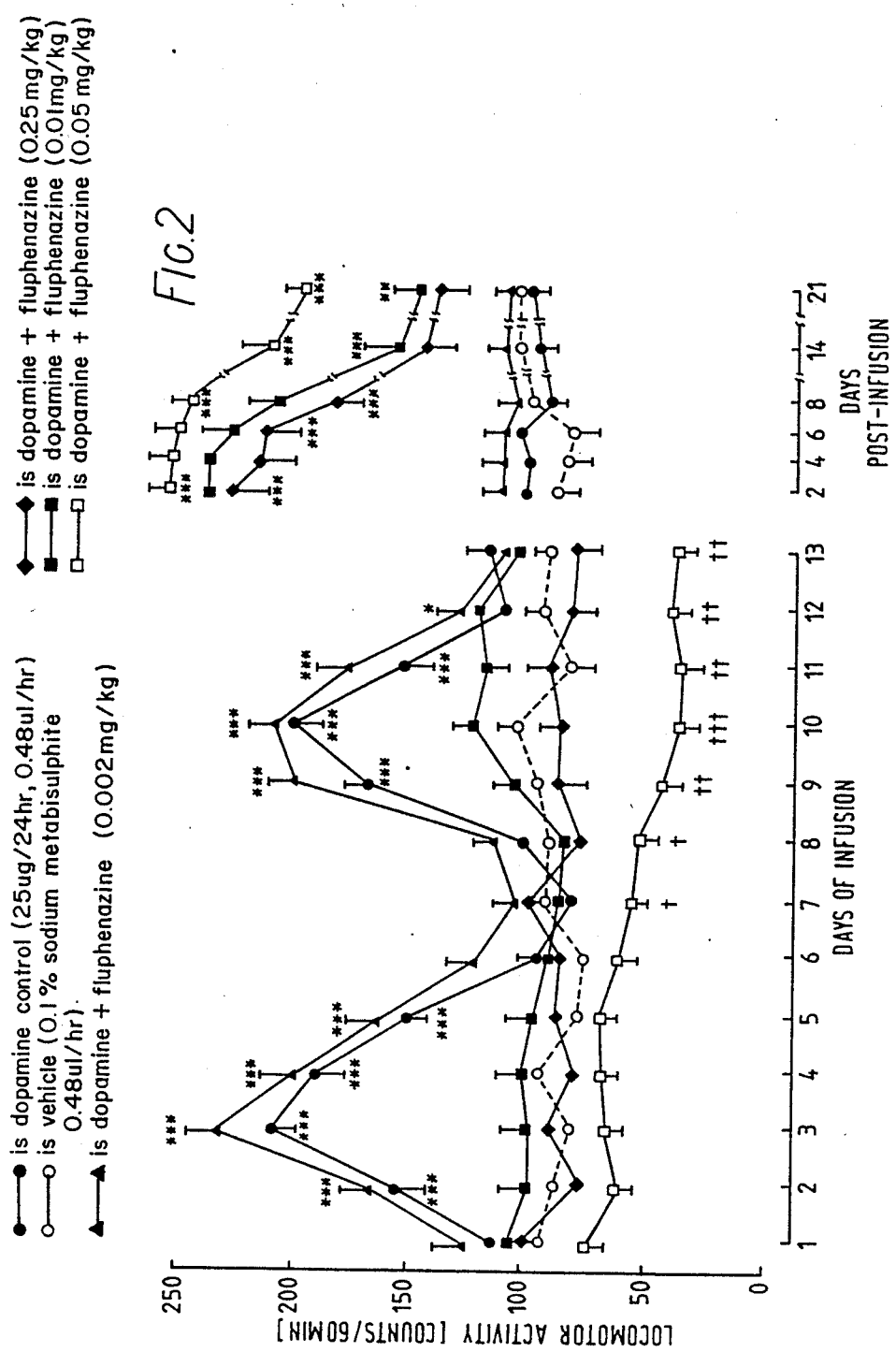

FIG. 2 shows the antagonism by fluphenazine of the hyperactivity caused by dopamine infused bilaterally into the rate nucleus accumbens. In FIG. 2:

◆——◆ is dopamine control (25 ug/24 hr, 0.48 ul/hr)

○——○ is vehicle (0.1% sodium metabisulphite), 0.48 ul/hr)

▲——▲ is dopamine+fluphenazine (0.002 mg/kg)

◆——◆ is dopamine+fluphenazine (0.025 mg/kg)

■——■ is dopamine+fluphenazine (0.01 mg/kg)

□——□ is dopamine+fluphenazine (0.05 mg/kg)

n=6, S.E.M.s given. Significant elevation of locomotor activity by dopamine (compared to vehicle) is indicated by *P less than 0.01, ***P less than 0.001.

Reduction in locomoter responding to values below control is indicated by +P less than 0.05, ++P less than 0.01, +++P less than 0.001. The significance of this rebound hyperactivity is indicated as P less than 0.01, *P less than 0.001 (two-way ANOVA followed by Dunnett's test for multiple comparisons).

Dopamine (25 ug/24 hr) infused slowly and persistently into the rat nucleus accumbens over a 13 day period caused biphasic hyperactivity with peaks of enhanced responding between days 2 and 5 and 9–12. This hyperactivity response could be antagonised by AGN 2979 at doses of 0.01– mg/kg i.p. given twice daily. At a lower dose of 0.00001 mg/kg b.d. the second peak of hyperactivity was prevented but control of the first peak of hyperactivity by this low dose of AGN 2979 was irregular (FIG. 1). Persistent or excessive motor depression was not observed on treatment with any dose of AGN 2979.

Fluphenazine also controlled the hyperactivity caused by dopamine infusion into the rat nucleus accumbens. Effective doses ranged from 0.025–0.05 mg/kg i.p. b.d. (FIG. 2). A dose of fluphenazine as low as 0.002 mg/kg i.p. b.d. failed to antagonise the peaks of hyperactivity caused by the mesolimbic dopamine excess (FIG. 2). At the high dose of fluphenazine, after 6 days of continued treatment, not only was the dopamine response antagonised, but locomotion was significantly depressed to values below control levels (FIG. 2).

Following withdrawal from treatment with fluphenazine (at those doses which controlled the dopamine response) and dopamine a marked rebound hyperactivity developed. At the highest doses this rebound response persisted throughout the 3 week post-infusion period (FIG. 2). In contrast, following withdrawal from treatment with AGN 2979 and dopamine a rebound hyperactivity was never observed (FIG. 1).

What is claimed is:

1. A method of treatment of psychosis which comprises administering to a patient suffering a psychotic disorder an anti-psychotic effective amount of a compound of the following Formula I.

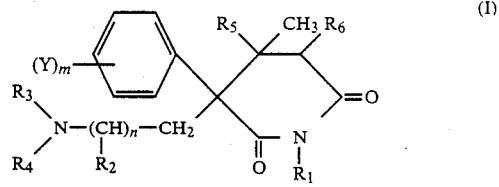

wherein:

$R_1$ represents hydrogen or $C_1$–$C_4$ alkyl;

n is 1 or 2;

$R_2$ represents hydrogen or methyl, provided that one $R_2$ is hydrogen when n is 2;

$R_3$ represents hydrogen or $C_1$–$C_2$ alkyl;

$R_4$ represents $C_1$–$C_2$ alkyl;

$R_5$ and $R_6$ independently represent hydrogen or methyl;

m is 0 to 3; and each X is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position, or a pharmacologically acceptable salt thereof.

2. The method according to claim 1, wherein the compound has the following Formula IA.

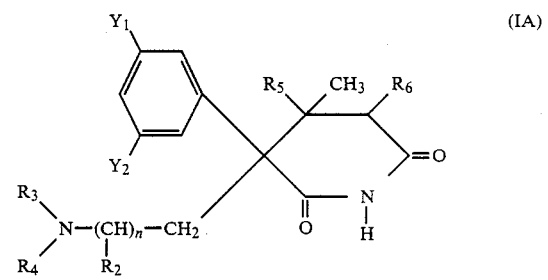

wherein:

n is 1 or 2;

$R_2$ represents hydrogen or methyl, provided that one $R_2$ is hydrogen when n is 2;

$R_3$ represents hydrogen or $C_1$–$C_2$ alkyl;

$R_4$ represents $C_1$–$C_2$ alkyl;

$R_5$ and $R_6$ independently represent hydrogen or methyl; and $Y_1$ and $Y_2$ independently represent hydrogen, hydroxy or $C_1$–$C_2$ alkoxy, or a pharmacologically acceptable salt thereof.

3. The method according to claim 2, wherein the compound has the following Formula IB.

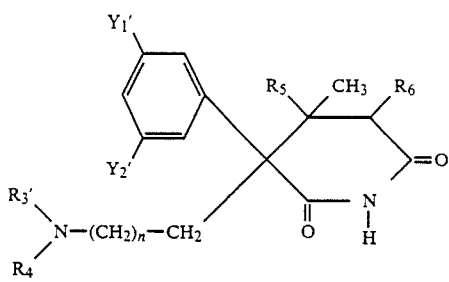
(IB)

wherein:
n is 1 or 2;
$R_3'$ and $R_4$ independently represent $C_1$-$C_2$ alkyl;
$R_5$ and $R_6$ independently represent hydrogen or methyl;

$Y_1'$ represents hydroxy or $C_1$-$C_2$ alkoxy; and
$Y_2'$ represents hydrogen, hydroxy or $C_1$-$C_2$ alkoxy, or a pharmacologically acceptable salt thereof.

4. The method according to claim 1, wherein the compound is 3-(3'-methoxyphenyl)-3-(3''-N,N-dimethylaminopropyl)-4,4-dimethyl-2,6-dixopiperidine.

5. The method according to claim 4, wherein the compound is the minus isomer.

6. The method according to claim 1, wherein the said anti-psychotic effective amount is about $10^{-5}$ mg/kg to about $10^2$ mg/kg.

7. The method according to claim 6, wherein the said anti-psychotic effective amount is about $10^{-4}$ mg/kg to about $10^2$ mg/kg.

8. The method according to claim 7, wherein the effective amount is about $10^{-3}$ to $10^{-1}$ mg/kg of the said compound.

* * * * *